United States Patent
Denker et al.

(10) Patent No.: US 6,917,833 B2
(45) Date of Patent: Jul. 12, 2005

(54) OMNIDIRECTIONAL ANTENNA FOR WIRELESS COMMUNICATION WITH IMPLANTED MEDICAL DEVICES

(75) Inventors: Stephen Denker, Mequon, WI (US); Arthur J. Beutler, Greendale, WI (US)

(73) Assignee: Kenergy, Inc., Mequon, WI (US)

( * ) Notice: Subject to any disclaimer, the term of this patent is extended or adjusted under 35 U.S.C. 154(b) by 114 days.

(21) Appl. No.: 10/663,957

(22) Filed: Sep. 16, 2003

(65) Prior Publication Data

US 2005/0060011 A1 Mar. 17, 2005

(51) Int. Cl.$^7$ ............................................. A61N 1/00
(52) U.S. Cl. ...................... 607/60; 607/32; 128/903
(58) Field of Search ......................... 607/2, 4, 9, 30, 607/32, 60; 128/903

(56) References Cited

U.S. PATENT DOCUMENTS

| | | | | |
|---|---|---|---|---|
| 5,713,939 A | | 2/1998 | Nedungadi et al. | 607/33 |
| 5,739,795 A | | 4/1998 | Chanteau et al. | 343/795 |
| 5,741,316 A | | 4/1998 | Chen et al. | 607/61 |
| 5,814,089 A | | 9/1998 | Stokes et al. | 607/32 |
| 5,995,874 A | | 11/1999 | Borza | 607/61 |
| 6,026,818 A | * | 2/2000 | Blair et al. | 128/899 |
| 6,067,474 A | | 5/2000 | Schulman et al. | 607/57 |
| 6,138,681 A | | 10/2000 | Chen et al. | 128/899 |
| 6,141,588 A | * | 10/2000 | Cox et al. | 607/9 |
| 6,167,312 A | * | 12/2000 | Goedeke | 607/60 |
| 6,298,271 B1 | * | 10/2001 | Weijand | 607/60 |
| 6,431,175 B1 | | 8/2002 | Penner et al. | 128/899 |
| 6,442,413 B1 | | 8/2002 | Silver | 600/345 |
| 6,445,953 B1 | | 9/2002 | Bulkes et al. | 607/33 |
| 2002/0005719 A1 | | 1/2002 | Gilboa et al. | 324/309 |
| 2002/0128546 A1 | | 9/2002 | Silver | 600/365 |

* cited by examiner

*Primary Examiner*—Carl Layno
(74) *Attorney, Agent, or Firm*—George E. Haas; Quarles & Brady LLP

(57) ABSTRACT

Medical devices implanted in a patient can be activated and powered by an RF signal. Unless the medical device is properly oriented with respect to the transmitting antennas enough signal energy may not be received to power that device. However, optimum orientation can not be assured due to constraints on the implantation position. The present transmitting antenna is flat and omnidirectional thereby eliminating the need to properly orient the implanted medical device.

29 Claims, 2 Drawing Sheets

OMNIDIRECTIONAL ANTENNA FOR WIRELESS COMMUNICATION WITH IMPLANTED MEDICAL DEVICES

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to apparatus for transmitting a radio frequency signal to a medical device implanted in an animal, and more particularly to cardiac pacing devices in which the radio frequency signal causes the implanted device to deliver energy to cardiac tissue for the purpose of stimulating contractions.

2. Description of the Related Art

A remedy for people with slowed or disrupted natural heart beating is to implant a cardiac pacing device. A cardiac pacing device is a small electronic apparatus that stimulates the heart to beat at regular intervals. That device consists of a pulse generator, implanted in the patient's chest, which produces electrical pulses that stimulate heart contractions. Electrical wires extend from the pulse generator to several electrodes placed adjacent specific muscles of the heart, which when electrically stimulated produce contraction of the adjacent heart chambers.

It is quite common that the wires extend through arteries or veins which enter the heart so that the electrodes can be placed in the muscle of the heart chamber requiring stimulation. The wires typically extend for some distance through the arteries or veins and may pass through one or two heart valves. In other patients, patch electrodes are placed on the exterior heart surface with wires extending through tissue to the pacing device. With either type of wire placement, it is important that the electrodes be attached to the proper positions on the heart to stimulate the muscles and produce contractions. Thus, it is desirable to properly locate the electrodes for maximum heart stimulation with minimal adverse impact to other physiological functions, such as blood circulation.

More recently wireless pacing devices have been proposed, such as the one described in U.S. Pat. No. 6,445,953. With this type of device, a radio frequency (RF) signal is transmitted from a conventional pacing circuit to stimulator devices placed on the heart at locations where stimulation is to occur. For example, the stimulator device can be mounted on a stent that is implanted in a blood vessel of the heart. The radio frequency signal activates the stent which applies an electrical stimulation pulse to the heart tissue. Electrical power for stimulating the heart is derived from the energy of the radio frequency signal.

One of the difficulties in this wireless system is ensuring that a maximum amount of the RF energy is received by the stimulator device. In the case of a stent, the antenna is a coil located on a cylindrical surface and receives the greatest amount of energy from an electromagnetic field oriented in a direction through the turns of the coil. However, since the stent can be implanted in different orientations in the patient's body and the orientation of the transmitter antenna similarly varied, it is difficult to ensure that the electromagnetic field from the RF signal will be properly oriented with respect to the stent antenna.

SUMMARY OF THE INVENTION

An antenna assembly is provided for transmitting a radio frequency signal to activate a device implanted in an animal. The antenna assembly has a substantially planar structure comprising a first antenna, a second antenna and a third antenna stacked on top of one another. The first antenna emits a first electromagnetic wave that propagates along a first axis, and the second antenna emits a second electromagnetic wave that propagates along a second axis which is substantially orthogonal to the first axis. The third antenna emits a third electromagnetic wave that propagates along a third axis which is substantially orthogonal to the first axis and the second axis.

Thus electromagnetic waves are emitted omnidirectionally from the antenna assembly and the receiving medical device can derive energy from the electromagnetic waves regardless of the orientation of the medical device to the transmitting apparatus.

In a preferred embodiment of the antenna assembly, the first antenna has a first coil section on one side of a first axis of symmetry and a second coil section located on another side of the first axis of symmetry. The second antenna includes a third coil section on one side of a second axis of symmetry and a fourth coil section on another side of the second axis of symmetry; wherein the second axis of symmetry is orthogonal to the first axis of symmetry. Preferably, the signal being transmitted is applied to the first antenna ninety degrees out of phase with the signal applied to the second antenna. This emits a circularly polarized RF signal from the first and second antennas. The third antenna has a conductive single coil section that emits the third electromagnetic wave that propagates orthogonally to the circularly polarized RF signal.

DETAILED DESCRIPTION OF THE INVENTION

Figure 1:
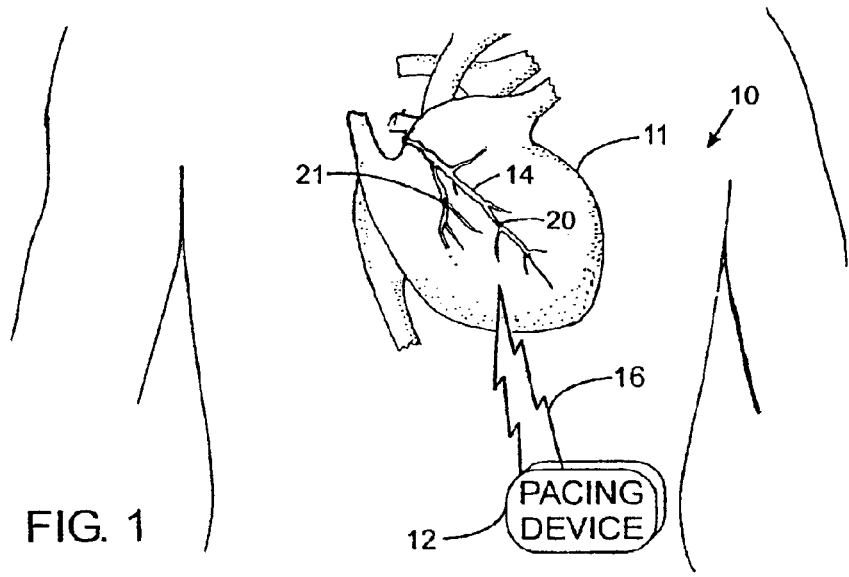
FIG. 1 depicts a cardiac pacing apparatus implanted in a patient.

With initial reference to FIG. 1, an apparatus 10 for applying electrical stimulation to pace a heart 11 comprises a pacing device 12 and one or more vascular electrode-stents 20 and 21 located in arteries or veins 14 through which blood flows to or from the heart muscles. As will be described in greater detail, the pacing device 12 emits a radio frequency signal 16 which produces an electric current in the implanted vascular electrode-stents, thereby stimulating the heart muscle.

Figure 2:
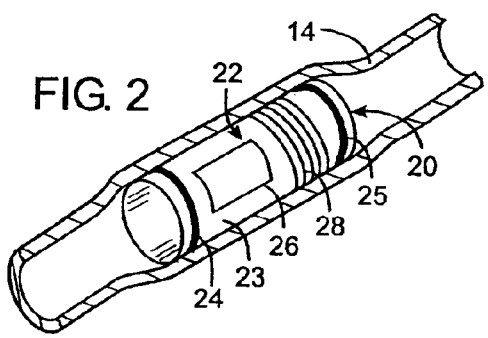
FIG. 2 is an isometric, cut-away view of a blood vessel with a vascular electrode-stent of the cardiac pacing apparatus.

Referring to FIG. 2, an electrode-stent 20 is placed in the artery or vein 14 of the heart 11. The body 23 of the electrode-stent 20 has a design similar to well-known expandable vascular stents that are employed to enlarge a restricted blood vessel. Such vascular stents have a generally tubular design that initially is collapsed to a relatively small diameter enabling them to pass freely through an artery or vein of a patient.

The procedure for implanting the electrode-stent 20 is similar to that used for conventional vascular stents. For example, the balloon at the end of a standard catheter is inserted into the electrode-stent 20 in a collapsed, or reduced diameter, configuration. That assembly then is inserted through an incision in a vein or artery near the skin of a patient and threaded through the vascular system to the appropriate location adjacent the heart 11. Specifically, the electrode-stent 20 ultimately is positioned in a cardiac artery or vein 14 adjacent to a section of the heart muscle where stimulation should be applied. The balloon of the catheter then is inflated to expand the vascular electrode-stent 20 which expansion also slightly enlarges the artery or vein 14, as seen in FIG. 2 which embeds the electrode-stent 20 in the wall of the blood vessel. This slight enlargement of the artery or vein 14 and the tubular design of the electrode-stent allows blood to flow relatively unimpeded through the device. The balloon is deflated, the catheter is removed from the patient, and the incision is closed. The electrode-stent 20 remains in the artery or vein without any wire connecting an electrode to pacing device 12.

Figure 3:
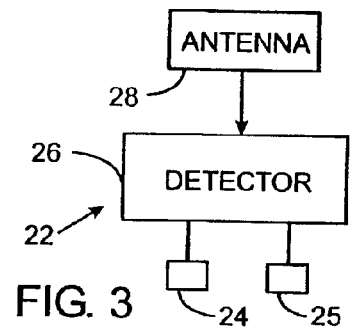
FIG. 3 is a schematic block diagram of an electrical circuit on the vascular electrode-stent.

With reference to FIGS. 2 and 3, the vascular electrode-stent 20 has a body 23 on which a signal receiving circuit 22 is mounted. The signal receiving circuit 22 includes an antenna 28, a radio frequency signal detector 26, and a stimulator, that is formed by first and second electrodes 24 and 25, for example. The antenna 28 comprises a coil having a plurality of turns and is connected to an input of the radio frequency signal detector 26 that may be tuned to the frequency (e.g. 27 MHz.) of the RF signal 16 emitted by the pacing device 12, but does not necessarily have to be a tuned circuit. Upon detecting the radio frequency signal 16, the detector 26 converts the energy of that signal into a differential voltage pulse that is applied to the first and second electrodes 24 and 25. Those electrodes form an electric circuit path with the patient's heart tissue allowing for stimulation of that tissue. Thus, each time the pacing device 12 emits a radio frequency signal 16, a pulse of electrical voltage is produced in the vicinity of the electrode-stent 20, thereby stimulating the heart muscle adjacent that electrode.

Figure 4:
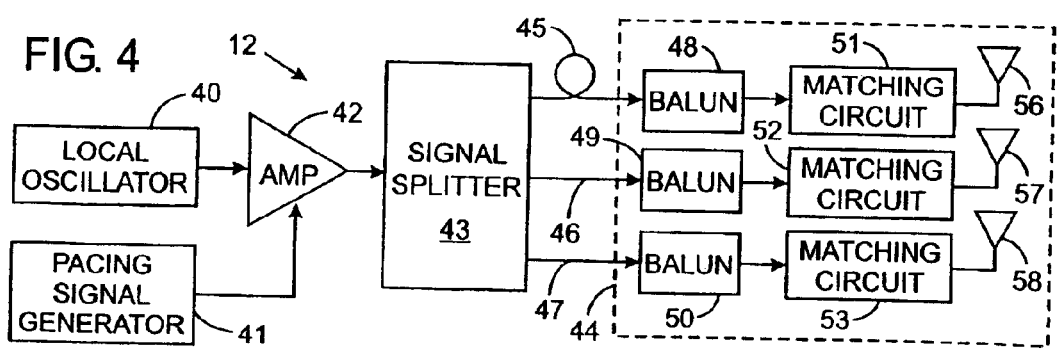
FIG. 4 is a schematic block diagram of the pacing device in FIG. 1 which incorporates the present invention.

Of particular interest to the present invention is the pacing device 12 illustrated in detail in FIG. 4. In large part the internal circuitry and operation of the pacing device is similar to that of prior cardiac pacers. However, instead of the pacing signal being applied to stimulation electrodes via wires, a radio frequency signal is produced. The pacing device 12 is powered by a battery (not shown).

The pacing device 12 contains a local oscillator 40 that produces the radio frequency signal at the predefined frequency (e.g. 27 MHz.) used by the cardiac pacing apparatus 10. This radio frequency signal is applied to the input of an amplifier 42 which is gated by a trigger signal from a conventional pacing signal generator 41. The circuitry of the pacing signal generator 41 is the same as that used in prior medical equipment to determine when a heart stimulation pulse is required. The output signal resulting from that determination enables the amplifier 42 to pass a burst of the radio frequency signal from the local oscillator 40.

The output from the amplifier 42 is connected to the input of a signal splitter 43 which divides the radio frequency signal into three signal portions of equal power. Each signal portion is transmitted to an antenna assembly 44 through a separate transmission line 45, 46 and 47, such as individual coaxial cables having a center conductor and a shield conductor. The first transmission line 45 is longer than the second transmission line 46, so that the respective signals at their antenna ends are ninety degrees out of phase.

Because the shield conductors are grounded only at the end proximate the signal splitter 43, the antenna end is not at ground potential due to the inductance of the shield conductor. This could form standing waves in the transmission lines 45–47 which dissipate energy that otherwise would be transmitted to the antenna assembly 44. As a consequence, each transmission lines 45–47 is provided with a separate balun 48, 49 or 50 in the antenna assembly 44. The baluns 48–50 separate the grounds of the transmission lines, thus providing a high impedance at the antenna end of the shields to attenuate any standing waves. For example, the balun may be formed by a helix of a coaxial transmission line of five turns with a capacitor connected across the shield conductor at the first and last turn, however other types of baluns can be used. The balun is a LC parallel resonator tuned to the frequency of the RF signal. After passing through the baluns 48–50, each transmission line 45, 46 or 47 is coupled by a matching circuit 51, 52 or 53 to one of three antennas 56, 57 or 58, respectively, to match the amplifier output impedance and the transmission line impedance to the input impedance of the respective antenna.

Figure 5:
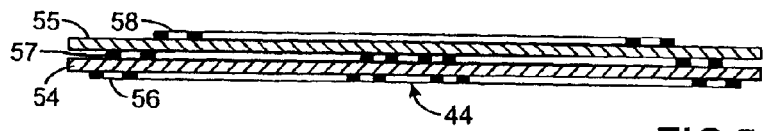
FIG. 5 is a cross sectional view through an antenna assembly of the pacing device.

Referring to FIG. 5, the three planar antennas 56, 57 or 58 of antenna assembly 44 are stacked one on top of the other in a multi-layer, laminated structure, that is circular with a diameter of 15–17 cm, for example. The first and second antennas 56 and 57 are formed by conductive stripes on opposite sides of a first substrate 54, while the third antenna 58 formed by a conductive stripes on a remote surface of a second substrate 55 that abuts the second antenna 57. However the second substrate 55 could be on the opposite side of the first substrate 54 thus abutting the first antenna 56. Each substrate is an electrically non-conductive material of a type conventionally used for rigid or flexible printed circuit boards and the conductive stripes are metal that is adhered to one or more surfaces of the substrate. The use of flexible substrates allows a externally worn antenna assembly 44 to bend slightly to conform to the outer surface of a patient's chest.

Figure 6:
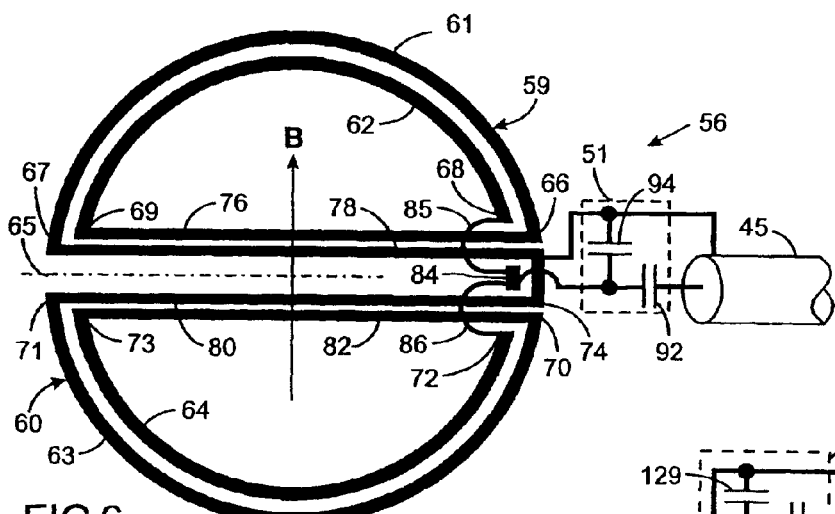
FIG. 6 illustrates a first antenna in the antenna assembly.

The conductive pattern of the first antenna 56 is illustrated in FIG. 6 and comprises a coil having first and second coil sections 59 and 60 located symmetrically on opposite sides of a first axis of symmetry 65. For example, each coil section 59 and 60 has two turns with each turn formed by a generally semicircular lobe and a linear conductor that is parallel to the first axis of symmetry 65. Coil sections with greater number of turns or even a single turn may also be used in given applications of the antenna assembly. Specifically, the first coil section 59 comprises a first conductive lobe 61 extending outward on one side of the first axis of symmetry 65 with a first end 66 and a second end 67 adjacent that axis, but spaced there from. A second lobe 62 of the first coil section 59 extends within and spaced from the first lobe 61 and has a third end 68 near the first end 66 and a fourth end 69 adjacent the second end 67 of the first lobe. A first linear conductor 76 connects the first end 66 of the first lobe 61 to the fourth end 69 of the second lobe 62, and a second linear conductor 78 connects the second end 67 of the first lobe to a first node 74. The first node 74 is on the first axis of symmetry 65 adjacent the first end 66 of the first lobe 61.

The second coil section 60 is formed by a third lobe 63 that extends outward on the opposite side of the first axis of symmetry 65 from the first coil section 59 and has a fifth end 70 adjacent to, but spaced from the first end 66 of the first lobe 61. The third lobe 63 has a sixth end 71. The fourth lobe 64 of the second coil section 60 is within the third lobe 63 and has a seventh end 72 adjacent the fifth end 70 of the third lobe and has an eighth end 73 that is adjacent to the sixth end 71. A third linear conductor 80 connects the sixth end 71 of the third lobe 63 to the first node 74. A fourth linear conductor 82 connects the eighth end 73 of the fourth lobe 64 to the fifth end of 70 of the third lobe 63.

The first node 74 is a short conductive element which partially fills the gap between the first end 66 of the first lobe 61 and the fifth end 70 of the third lobe 63. A second node 84, formed by another short conductive element, is located on the first axis of symmetry 65 adjacent to the first node 74 between the third and seventh ends 68 and 72 of the second and fourth lobes 62 and 63, respectively. The third end 68 of the second lobe 62 and the seventh end 72 of the fourth lobe 64 are electrically connected by insulated jumpers 85 and 86 to the second node 84. The first and second nodes 74 and 84 provide terminals for coupling the first transmission line 45 to the first and second coil sections 59 and 60 of the first antenna 56.

The first antenna 56 is connected by the first matching circuit 51 to the first transmission line 45. Specifically, the first matching circuit 51 has a first, or impedance matching, capacitor 92 which couples the center conductor of that transmission line to the second node 84 of the antenna. The first transmission line 45 also has a shield conductor that is connected directly to the first node 74 and a second, or tuning, capacitor 94 is connected between the first and second nodes 74 and 84. The coupling of the first transmission line to the first and second nodes 74 and 84, applies the radio frequency signal from the signal splitter 43 to the first antenna 56. This results in the first antenna 56 emitting an electromagnetic field B in the direction indicated by the arrow at the center of the antenna.

Figure 7:
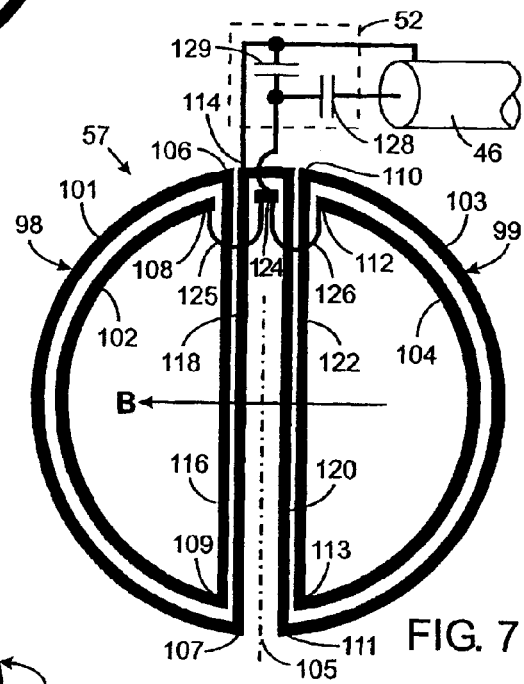
FIG. 7 shows a second antenna in the antenna assembly.

The conductive pattern of the second antenna 57 is illustrated in FIG. 7 and is identical to that of the first antenna 56 except that it is rotated ninety degrees on the first substrate 54. The second antenna 57 comprises third and fourth coil sections 98 and 99 opposite sides of a second axis of symmetry 105. For example, each of these coil sections 98 and 99 has two turns with each turn formed by a generally semicircular lobe and a linear conductor parallel to the second axis of symmetry 105. Specifically the third coil section 98 comprises a fifth conductive lobe 101 extending outward on one side of the second axis of symmetry 105 with a ninth end 106 and a tenth end 107 adjacent that axis, but spaced there from. A sixth lobe 102 of the third coil section 98 extends within and spaced from the fifth lobe 101 and has an eleventh end 108 near the ninth end 106 and a twelfth end 109 adjacent the tenth end 107 of the fifth lobe. A fifth linear conductor 116 connects the ninth end 106 of the fifth lobe 101 to the twelfth end 109 of the sixth lobe 102, and a sixth linear conductor 118 connects the tenth end 107 of the fifth lobe to a third node 114. The third node 114 is on the second axis of symmetry 105 adjacent the ninth end 106 of the fifth lobe 101.

The fourth coil section 99 is formed by a seventh lobe 103 that extends outward on the opposite side of the second axis of symmetry 105 from the third coil and has a thirteenth end 110 adjacent to, but spaced from ninth end 106 of the fifth lobe 101. The seventh lobe 103 has a fourteenth end 111. The eighth lobe 104 of the fourth coil section 99 is within the seventh lobe 103 and has a fifteenth end 112 adjacent the thirteenth end 110 of the seventh lobe and a sixteenth end 113 that is adjacent to the fourteenth end 111. A seventh linear conductor 120 connects the fourteenth end 111 of the seventh lobe 103 to the third node 114. An eighth linear conductor 122 connects the sixteenth end 113 of the eighth lobe 104 to the thirteenth end 110 of the seventh lobe 103.

The third node 114 is a short conductive element between the ninth and thirteenth ends 106 and 110 of the fifth and the seventh lobes 101 and 103, respectively. A fourth node 124 is a short conductive element located on the second axis of symmetry 105 adjacent to the third node 114 between the eleventh and fifteenth end ends 108 and 112 of the sixth and eighth lobes 102 and 104, respectively. The eleventh end 108 of the sixth lobe 102 and the fifteenth end 112 of the eighth lobe 104 are electrically connected by insulated jumpers 125 and 126 to the fourth node 124. The third and fourth nodes 114 and 124 provide terminals for coupling the second transmission line 46 to the third and fourth coil sections 98 and 99 of the second antenna 57.

The second antenna 57 is connected by the second matching circuit 52 to the second transmission line 46. Specifically, the second matching circuit 52 has one capacitor 128 which couple the center conductor of that transmission line to the fourth node 124 of the second antenna. The second transmission line 46 also has a shield conductor that is coupled directly to the third node 114 and another capacitor 129 is connected between the third and fourth node 114 and 124. The coupling of the second transmission line 46 to the third and fourth nodes 114 and 124 applies the radio frequency signal from the signal splitter 43 to the second antenna 57. This results in the second antenna 57 emitting an electromagnetic field B in the direction indicated by the arrow at the center of the antenna, which is orthogonal to the direction of the electromagnetic field generated by the first antenna 56.

Figure 8:
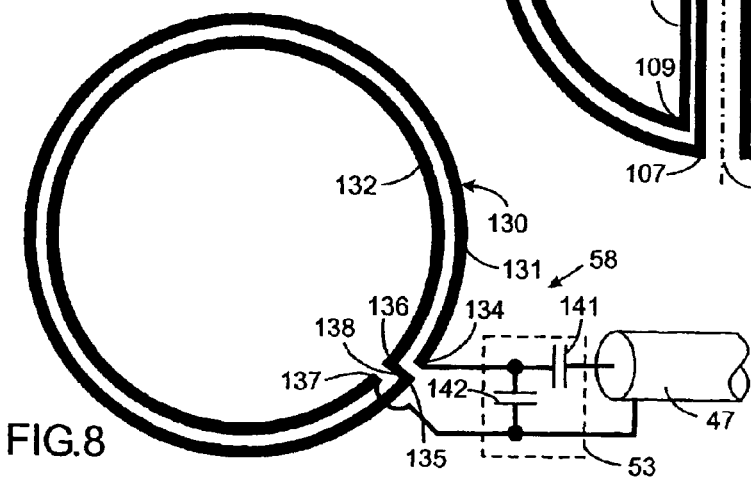
FIG. 8 illustrates a third antenna in the antenna assembly.

With reference to FIG. 8, the third antenna 58 comprises a single coil 130 with two turns formed by a pair of concentric, annular conductors 131 and 132 which preferably are circular. It should be understood that the third antenna 58 may have fewer or more turns depending on the particular application of the antenna assembly 44. The first annular conductor 131 has a gap, thereby forming seventeenth and eighteenth ends 134 and 135. The second annular conductor 132 is within the first annular conductor 131 and also has a gap, thereby creating nineteenth and twentieth ends 136 and 137. A bridging conductor 138 connects the eighteenth end 135 to the nineteenth end 136.

The third antenna 58 is connected to the third transmission line 47 by the third matching circuit 53, The center conductor of the third transmission line 47 is connected by a capacitor 141 to the seventeenth end 134 of the first annular conductor 132. The shield conductor of the third transmission line 47 is connected directly to the twentieth end 137. Another capacitor 142 is connected across the seventeenth end 134 and the twentieth end 137. The third antenna 58 emits an electromagnetic field B in a direction perpendicular to the plane of the drawing.

The radii of each lobe 101–104 of the second antenna 57 are different than the radii of the lobes 61–63 of the first antenna 56, so that the respective conductors do not lie over one another in the layered antenna assembly 44 as evident in FIG. 5. Similarly, the radii of the first and second annular conductors 131 and 132 of the third antenna 58 are shown different than the radii of the lobes in the other two antennas 56 and 57, so that its conductive pattern does not lie over either of the conductors of the antenna lobes. Offsetting the conductive elements of each of three planar antennas 56–58 in this manner, reduces the capacitive coupling between adjacent antennas. Alternatively, it may be possible that the conductive patterns of the first and third antennas lie over each other as the intermediate circuit board layers provide a substantial dielectric to impede detrimental capacitive coupling.

Referring again to FIG. 4, when the pacing signal generator 41 determines that a stimulation pulse is required, the amplifier 42 is triggered to pass a burst of the radio frequency signal from the local oscillator 40. The signal splitter 43 then divides the signal into three separate portions for the three antennas 56–58. The signal portions are applied through one combination of a balun 44–46 and a matching circuit 50–52 to the respective antenna 56–58 within assembly 44. Because the first transmission line 45 feeding the first antenna 56 is longer than the second transmission line 46 for the second antenna 57, the signal portion to the first antenna 56 is ninety degrees out of phase with respect to the signal portion that is applied to the second antenna 57. As a result, a circular polarized RF field, parallel to the plane of the antenna assembly 44, is generated by the first and second antennas 56 and 57. The circular polarized field in this plane is important in order to achieve an omnidirectional distribution of the RF field. If the first and second antennas 56 and 57 receive signals that were in phase, a linear field would be generated in a direction forty-five degrees with respect to the orientation of each antenna which would be same as would be achieved by a single antenna oriented in that direction.

The third signal portion, fed through the third balun 46 and the third matching circuit 52, is applied to the third antenna 58. The circular design of this antenna emits a radio frequency wave that propagates in a direction that is orthogonal to the circular polarized field produced by the other two antennas 56 and 57. As a result of the orientation of each of these emitted RF fields, the antenna assembly 44 forms an omnidirectional field which induces voltage into the circuitry on the implanted stent, independent of the orientation of the stent with respect to the transmitter antenna assembly 44.

The foregoing description was primarily directed to a preferred embodiment of the invention. Even though some attention was given to various alternatives within the scope of the invention, it is anticipated that one skilled in the art will likely realize additional alternatives that are now apparent from disclosure of embodiments of the invention. For example, although the invention has been described in the context of a cardiac pacing device, the novel antenna may be used with devices for electrically stimulating other organs of the body, such as the brain for seizure control. The present antenna may also be used to communicate with sensing devices implanted in an animal. Accordingly, the scope of the invention should be determined from the following claims and not limited by the above disclosure.

We claim:

1. In an apparatus for transmitting a radio frequency signal to activate a device implanted in an animal, an antenna assembly to which the radio frequency signal is applied and which has a substantially planar structure, the antenna assembly comprising a first antenna, a second antenna and a third antenna stacked on top of one another, wherein the first antenna produces a first electromagnetic field in a first direction, the second antenna produces a second electromagnetic field in a second direction which is substantially orthogonal to the first direction, and the third antenna produces a third electromagnetic field in a third direction which is substantially orthogonal to the first direction and the second direction.

2. The apparatus as recited in claim 1 wherein the first antenna has a first planar coil section on one side of a first axis and a second planar coil section located on another side of the first axis.

3. The apparatus as recited in claim 2 wherein the second antenna has a third planar coil section on one side of a second axis and a fourth planar coil section located on another side of the second axis, wherein the second axis is substantially orthogonal to the first axis.

4. The apparatus as recited in claim 3 wherein each of the first planar coil section, second planar coil section, third planar coil section, and fourth planar coil section comprises two coil turns.

5. The apparatus as recited in claim 3 wherein:
the first antenna further comprises a first node and a second node between which the first planar coil section and the second planar coil section are connected, and a first impedance matching circuit connected to the first node and a second node for coupling a transmission line to the first antenna; and
the second antenna further comprises a third node and a fourth node between which the third planar coil section and the fourth planar coil section are connected, and a second impedance matching circuit connected to the third node and a fourth node for coupling another transmission line to the second antenna.

6. The apparatus as recited in claim 3 wherein the third antenna has single planar coil having two ends.

7. The apparatus as recited in claim 6 further comprising an impedance matching circuit connected to the two ends for coupling a transmission line to the third antenna.

8. The apparatus as recited in claim 6 wherein the first antenna, the second antenna and the third antenna are different sizes so that their respective coil sections do not overlap.

9. The apparatus as recited in claim 1 wherein the first antenna has at least a first pair of conductive lobes with one conductive lobe extending on one side of a first axis and another conductive lobe extending on another side of the first axis.

10. The apparatus as recited in claim 9 wherein the second antenna has at least a second pair of conductive lobes with one conductive lobe of which extending on one side of a second axis and another conductive lobe of which extending on another side of the second axis.

11. The apparatus as recited in claim 10 wherein second axis is substantially orthogonal to the first axis.

12. The apparatus as recited in claim 1 wherein the third antenna comprises at least one conductive loop with a gap.

13. In apparatus for transmitting a radio frequency signal to a device implanted in an animal, an antenna assembly comprising:
a first antenna to which the radio frequency signal is applied to activate the medical device is applied and having a first coil section on one side of a first axis of symmetry and a second coil section located on another side of the first axis of symmetry;
a second antenna to which the radio frequency signal is applied to activate the medical device and having a third coil section on one side of a second axis of symmetry and a fourth coil section located on another side of the second axis of symmetry, wherein the second axis of symmetry is orthogonal to the first axis of symmetry; and a third antenna to which the radio frequency signal is applied to activate the medical device and having a conductive loop a gap.

14. The apparatus as recited in claim 13 wherein each of the first, second, third and fourth coil section comprises at least one curved lobe having two ends, and a linear conductor connected to one end and extending to a point adjacent the other end.

15. The apparatus as recited in claim 13 wherein the first coil section and the second coil section of the first antenna each have a plurality of turns.

16. The apparatus as recited in claim 15 wherein the third coil section and the fourth coil of the second antenna section each have a plurality of turns.

17. The apparatus as recited in claim 13 wherein the first antenna, the second antenna and the third antenna are stacked on top of one another in a flat assembly.

18. The apparatus as recited in claim 17 wherein each of the first, second, and third antennas has a center point with all the center points being substantially aligned.

19. The apparatus as recited in claim 17 wherein the respective coil sections of the first antenna, and the second antenna have curved lobes which do not overlap in the flat assembly.

20. The apparatus as recited in claim 13 wherein the first antenna and the second antenna are formed by conductive patterns on opposite sides of a first substrate, and the third antenna is formed by a conductive pattern on a second substrate that is parallel to the first substrate.

21. The apparatus as recited in claim 13 wherein the antenna assembly is substantially planar.

22. The apparatus as recited in claim 13 wherein the third antenna has a pair of concentric conductive loops, each having a gap.

23. The apparatus as recited in claim 13 further comprising a signal divider coupled to the first, second, and third antennas and dividing the pulsed signal into three portions each of which is applied to a different one of the antennas.

24. The apparatus as recited in claim 23 wherein the signal divider is coupled to each of the first, second, and third antennas by a balun and an impedance matching circuit.

25. The apparatus as recited in claim 23 wherein the signal divider is coupled to the first antenna by a mechanism wherein the portion of the pulsed signal which is applied to the first antenna is ninety degrees out of phase from the portion of the pulsed signal which is applied to the second antenna.

26. In an apparatus for transmitting a radio frequency signal to a device implanted in an animal, an antenna arrangement comprising:

a first antenna, a second antenna, and a third antenna each having a planar structure with one of the first, second, and third antennas located between the other two antennas;

each of the first antenna and the second antenna having a first lobe extending to one side of an axis and spaced apart first and second ends, a second lobe having spaced apart third and fourth ends and extending within the first lobe with the third end adjacent the first end, a third lobe extending to an opposite side of the first axis and having spaced apart fifth and sixth ends, a fourth lobe having spaced apart seventh and eighth ends and extending to the opposite side within the third lobe with the seventh end adjacent the fifth end, the first end of the first lobe is connected to the fourth end of the second lobe, the second end connected to a node between the first end of the first lobe and the fifth end of the third lobe and separated there from, the sixth end is connected to the node, and the third end of the second lobe is connected to the seventh end of the fourth lobe;

wherein the axis of the first antenna is orthogonal to the axis of the second antenna; and the third antenna having a first annular conductor with ninth and tenth ends with a gap there between, and a second annular conductor inside the first annular conductor and having eleventh and twelfth ends with another gap there between, wherein the tenth end is connected the eleventh end.

27. The apparatus as recited in claim 26 wherein the first and second lobes have a generally semicircular shape.

28. The apparatus as recited in claim 26 wherein each of the first and second antennas further comprises an impedance matching circuit connected to the node, the third end and the seventh end for coupling a transmission line to the respective antenna.

29. The apparatus as recited in claim 26 wherein third antenna further comprises an impedance matching circuit connected to the ninth end and the twelfth end for coupling a transmission line to the third antenna.

* * * * *